US012606709B2

(12) United States Patent
Akiyama et al.

(10) Patent No.: US 12,606,709 B2
(45) Date of Patent: Apr. 21, 2026

(54) METHOD FOR INCREASING SPECIFIC SURFACE AREA OF TITANIUM PHOSPHATE PLATE-SHAPED PARTICLES, AND POWDER CONTAINING PLATE-SHAPED PARTICLES DERIVED FROM TITANIUM PHOSPHATE

(71) Applicant: FUJIMI INCORPORATED, Kiyosu (JP)

(72) Inventors: Tomomi Akiyama, Kiyosu (JP); Takashi Hayakawa, Kiyosu (JP); Keiji Ashitaka, Kiyosu (JP); Naoya Miwa, Kiyosu (JP)

(73) Assignee: FUJIMI INCORPORATED, Kiyosu (JP)

( * ) Notice: Subject to any disclaimer, the term of this patent is extended or adjusted under 35 U.S.C. 154(b) by 1064 days.

(21) Appl. No.: 17/638,494

(22) PCT Filed: May 15, 2020

(86) PCT No.: PCT/JP2020/019493
§ 371 (c)(1),
(2) Date: Feb. 25, 2022

(87) PCT Pub. No.: WO2021/038979
PCT Pub. Date: Mar. 4, 2021

(65) Prior Publication Data
US 2022/0403178 A1 Dec. 22, 2022

(30) Foreign Application Priority Data

Aug. 28, 2019 (JP) ................................. 2019-156009
Aug. 28, 2019 (JP) ................................. 2019-156010
Aug. 28, 2019 (JP) ................................. 2019-156011

(51) Int. Cl.
| | |
|---|---|
| *C09C 1/36* | (2006.01) |
| *A61K 8/02* | (2006.01) |
| *A61K 8/29* | (2006.01) |
| *A61Q 1/02* | (2006.01) |
| *C09C 3/00* | (2006.01) |

(52) U.S. Cl.
CPC ................ *C09C 1/36* (2013.01); *A61K 8/022* (2013.01); *A61K 8/0254* (2013.01); *A61K 8/29* (2013.01); *A61Q 1/02* (2013.01); *C09C 3/003* (2013.01); *A61K 2800/43* (2013.01); *A61K 2800/60* (2013.01); *C01P 2004/03* (2013.01); *C01P 2004/24* (2013.01); *C01P 2004/54* (2013.01); *C01P 2004/61* (2013.01); *C01P 2004/62* (2013.01); *C01P 2004/64* (2013.01); *C01P 2006/12* (2013.01)

(58) Field of Classification Search
CPC ........... C09C 1/36; C09C 3/003; A61K 8/022; A61K 8/0254; A61K 8/29; A61K 2800/43; A61K 2800/60; A61K 8/24; A61Q 1/02; C01P 2004/03; C01P 2004/24; C01P 2004/54; C01P 2004/61; C01P 2004/62; C01P 2004/64; C01P 2006/12; C01B 25/372; C01B 25/37
See application file for complete search history.

(56) References Cited

U.S. PATENT DOCUMENTS

| | | | |
|---|---|---|---|
| 3,558,273 | A | 1/1971 | Beck et al. |
| 2020/0377369 | A1 | 12/2020 | Iwakuni et al. |

FOREIGN PATENT DOCUMENTS

| | | | |
|---|---|---|---|
| AU | 5724969 | A | 1/1971 |
| CN | 104477870 | A | 4/2015 |
| CN | 105271158 | A | 1/2016 |
| FR | 2054705 | A | 5/1971 |
| GB | 1 282 594 | A | 7/1972 |
| JP | S49-001720 | B2 | 1/1974 |
| WO | WO-2018/180797 | A1 | 10/2018 |

OTHER PUBLICATIONS

Satya Kishore et al., "Electrochemical intercalation of lithium in the titanium hydrogeno phosphate Ti(HPO4)2.H2O" Journal of Power Sources 169, Mar. 2007, 355-360 (Year: 2007).*
Nunes, L, M. et al., "Some features of crystalline α-titanium hydrogenphosphate, modified sodium and n-butylammonium forms and thermodynamics of ionic exchange with K+ and Ca2+", Thermochimica Acta, 1999, vol. 328, pp. 297-305.
Guo, S. et al., "Synthesis of shape-controlled mesoporous titanium phosphate nanocrystal: The hexagonal titanium phosphate with enhanced hydrogen generation from water splitting", International Journal of Hydrogen Energy, Dec. 25, 2013, vol. 39, pp. 2446-2453.
European Search Report on EP Appl. Ser. No. EP 20858867 dated Sep. 29, 2022 (7 pages).
International Preliminary Report on Patentability on PCT Appl. Ser. No. PCT/JP2020/019493 dated Mar. 10, 2022 (7 pages).

* cited by examiner

*Primary Examiner* — Anthony J Zimmer
*Assistant Examiner* — Abdul-Rahman Yusuf Waleed Smari
(74) *Attorney, Agent, or Firm* — Foley & Lardner LLP

(57) ABSTRACT

A method for increasing the specific surface area of titanium phosphate plate-shaped particles of this invention includes: obtaining a liquid in a state where a powder containing titanium phosphate plate-shaped particles is dispersed in an aqueous alkaline solution.

12 Claims, 4 Drawing Sheets

METHOD FOR INCREASING SPECIFIC SURFACE AREA OF TITANIUM PHOSPHATE PLATE-SHAPED PARTICLES, AND POWDER CONTAINING PLATE-SHAPED PARTICLES DERIVED FROM TITANIUM PHOSPHATE

TECHNICAL FIELD

The present invention relates to a method for increasing the specific surface area of titanium phosphate plate-shaped particles and a powder containing plate-shaped particles derived from titanium phosphate.

BACKGROUND ART

PTL 1 describes a titanium phosphate powder containing plate-shaped particles (plate crystal particles) of titanium phosphate and a method for manufacturing the same. This titanium phosphate powder has an average thickness of the plate-shaped particles of 0.01 μm or more and less than 0.10 μm and an aspect ratio, which is a value obtained by dividing the average primary particle diameter of the plate-shaped particles by the average thickness, of 5 or more. The titanium phosphate containing such thin plate-shaped particles has good slipperiness between the particles, and therefore is suitable as additives to be added to cosmetic materials (for example, white pigments for cosmetic materials) or pigments to be added to paints.

According to the manufacturing method described in PTL 1, a titanium phosphate powder having an average thickness of 0.4 to 0.8 μm and a particle diameter (average primary particle diameter) of 3 to 7 μm can also be obtained. In that case, the specific surface area of plate-shaped particles constituting the obtained titanium phosphate powder is 2 to 3 $m^2/g$, for example. The specific surface area of the titanium phosphate plate-shaped particles obtained by this method changes depending on the particle size and the thickness. When changing the specific surface area of the titanium phosphate plate-shaped particles, the particle size is changed while holding the aspect ratio, for example.

CITATION LIST

Patent Literature

PTL 1: WO 2018/180797

SUMMARY OF INVENTION

Technical Problem

However, when the particle size is changed to change the specific surface area of the titanium phosphate plate-shaped particles, the physical properties determined by the particle size, e.g., slipperiness (average friction coefficient (MIU)), of the titanium phosphate plate-shaped particles change. Therefore, it is difficult to obtain titanium phosphate plate-shaped particles in which both the specific surface area and the physical properties, such as slipperiness, have desired values.

Further, the titanium phosphate powder described in PTL 1 has room for improvement in terms of a refreshing feeling when used as a powder for cosmetic materials.

It is a first object of the present invention to provide a method for increasing the specific surface area of titanium phosphate plate-shaped particles capable of increasing the specific surface area without changing the particle size.

It is a second object of the present invention to provide a powder having an excellent refreshing feeling when used as a powder for cosmetic materials.

It is a third object of the present invention to provide a powder having both slipperiness and a refreshing feeling when used as a powder for cosmetic materials.

Solution to Problem

A first aspect of the present invention is a method for increasing the specific surface area of titanium phosphate plate-shaped particles including: obtaining a liquid in a state where a powder containing titanium phosphate plate-shaped particles is dispersed in an aqueous alkaline solution.

A second aspect of the present invention is a powder satisfying the following configurations (1) and (2) of:

(1) containing plate-shaped particles derived from titanium phosphate containing any of a compound derived from titanium phosphate in which hydrogen of the titanium phosphate is replaced with alkali metal or a compound derived from titanium phosphate in which alkali metal is contained in crystals of the titanium phosphate; and (2) having a ratio of an actual specific surface area to an assumed specific surface area (Actual specific surface area/Assumed specific surface area) of 1.5 or more, the actual specific surface area being the specific surface area of the plate-shaped particles derived from titanium phosphate measured by a gas adsorption method, and the assumed specific surface area being the specific surface area measured by assuming the outer surface as a plane from the average particle size and the average thickness of the plate-shaped particles derived from titanium phosphate obtained by microscopic observation.

A third aspect of the present invention is a powder satisfying the configuration (1) above and the following configuration (3) of:

(3) having a ratio of the average deviation of the friction coefficient (MMD) to the average friction coefficient (MIU) (MMD/MIU) of 0.011 or more.

Advantageous Effects of Invention

According to the method of the first aspect of the present invention, the specific surface area can be increased without changing the particle size of the titanium phosphate plate-shaped particles.

The second aspect of the present invention can provide a powder having an excellent refreshing feeling when used as a powder for cosmetic materials.

The third aspect of the present invention can provide a powder achieving both slipperiness and a refreshing feeling when used as a powder for cosmetic materials.

DESCRIPTION OF EMBODIMENTS

Figure 1A:
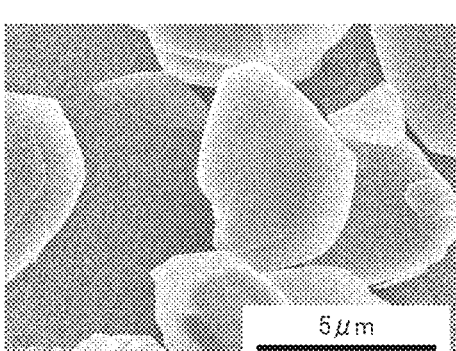
FIGS. 1A and 1B are SEM images of plate-shaped particles constituting powders of Samples No. 1-1, No. 4-1, No. 5-1 obtained in Examples.

Embodiments of the present invention will now be described in detail. The embodiments described below describe examples of the present invention and the present invention is not limited to the embodiments. Further, the embodiments described below can be variously altered or modified and embodiments obtained by such alterations or modifications may also be included in the present invention.

First Embodiment

A method for increasing the specific surface area of titanium phosphate plate-shaped particles of this embodiment includes a first step of obtaining a liquid in a state where a powder containing titanium phosphate plate-shaped particles is dispersed in an aqueous alkaline solution and having a pH around neutrality, a second step of separating the particles from the liquid (dispersion liquid of the particles), and a third step of drying the separated particles.

In the first step, the powder containing titanium phosphate plate-shaped particles is first dispersed in the aqueous alkaline solution. As methods therefor, the following four methods are mentioned, for example.

A first method is a method in which the aqueous alkaline solution is added to or a compound exhibiting alkalinity when melted in water is added to and mixed with a dispersion liquid in which the powder containing titanium phosphate plate-shaped particles is dispersed in water (hereinafter, also referred to as "titanium phosphate dispersion liquid"). A second method is a method including placing the powder containing titanium phosphate plate-shaped particles in a vessel, and then adding the aqueous alkaline solution to the vessel, followed by mixing.

A third method is a method in which the dispersion liquid in which the powder containing titanium phosphate plate-shaped particles is dispersed in water is added to or the powder containing titanium phosphate plate-shaped particles is added to and mixed with the aqueous alkaline solution. A fourth method is a method including placing a compound exhibiting alkalinity when melted in water in a vessel, and then placing the dispersion liquid in which the powder containing titanium phosphate plate-shaped particles is dispersed in water in the vessel, followed by mixing.

As the powder containing titanium phosphate plate-shaped particles, a powder is used which contains hexagonal plate-shaped particles and has an average thickness of 0.01 μm or more and 4 μm or less, an average primary particle diameter of 0.05 μm or more and 20 μm or less, and an aspect ratio, which is a value obtained by dividing the average primary particle diameter by the average thickness, of 5 or more.

As the aqueous alkaline solution, an aqueous sodium hydroxide solution, an aqueous potassium hydroxide solution, an aqueous sodium carbonate solution, and an aqueous potassium carbonate solution are used, for example. As the compound exhibiting alkalinity when melted in water, sodium carbonate or potassium carbonate is used, for example.

In the first step, protons of titanium phosphate are replaced with alkali metal ions to cause a neutralization reaction. With the progress of this neutralization reaction, the pH of the aqueous alkaline solution decreases or the pH of the titanium phosphate dispersion liquid increases. When the neutralization reaction is completed, the pH reaches a stabilized value around neutrality (for example, 5 or more and 9 or less). The mixing is continued until this state is reached or the mixture is left to stand after the mixing. The standing time when the mixture is left to stand after the mixing changes depending on the atmospheric temperature, but is suitably about 2 hours in the case of room temperature (25° C.)

In the first step, irregularities are formed on the surface of the titanium phosphate plate-shaped particles. As a result, the specific surface area of the titanium phosphate plate-shaped particles increases, while the particle size remains unchanged. This specific surface area is not a specific surface area measured by assuming the surface of the titanium phosphate plate-shaped particles as a plane (assumed specific surface area), but a specific surface area measured as a value including the area of surfaces formed by surface irregularities or internal holes (actual specific surface area).

The higher the pH of the liquid obtained in the first step, the higher the formation degree of the surface irregularities of the titanium phosphate plate-shaped particles. However, when the pH is excessively high, the possibility is high that the shape of the titanium phosphate plate-shaped particles is collapsed. Therefore, the conditions of the first step are preferably set to cause a neutralization reaction in which the pH is stabilized within the range of 5 or more and 9 or less.

In the second step, centrifugation or suction filtration, for example, is performed to separate the titanium phosphate plate-shaped particles (strictly, plate-shaped particles derived from titanium phosphate) having a specific surface area increased by the first step and water from each other.

In the third step, the separated particles are dried until a powder state is reached. The drying time changes depending on the drying temperature and is suitably about 1 day in the case of 105° C.

According to the method of this embodiment, the specific surface area of the titanium phosphate hexagonal plate-shaped particles having an average thickness of 0.01 μm or more and 4 μm or less, an average primary particle diameter of 0.05 μm or more and 20 μm or less, and an aspect ratio (value obtained by dividing the average primary particle diameter by the average thickness) of 5 or more can be increased without changing the particle size.

Therefore, the hexagonal plate-shaped particles constituting the obtained powder have a large specific surface area, but the particle size and the thickness do not change, and therefore the state where the aspect ratio is 5 or more and the average thickness is 4 μm or less is held. More specifically, both the specific surface area and the slipperiness (average friction coefficient (MIU)) of the titanium phosphate plate-shaped particles can be set to desired values.

According to the method of this embodiment, the particle size and the thickness of the titanium phosphate hexagonal plate-shaped particles do not change by the treatment performed in the first step, and therefore the assumed surface area (for example, surface area calculated as a value obtained by assuming the crystal particle as an ideal hexagonal column and totalizing the areas of the eight surfaces constituting the hexagonal column based on the particle size and the thickness by image analysis of micrographs) does not change before and after the first step. However, the actual surface area (total value of the areas of all surfaces including surfaces of the surface irregularities and the internal holes of the titanium phosphate hexagonal plate-shaped particles) increases after the first step. Also with respect to the specific surface area which is the surface area per unit mass, the assumed specific surface area which is the "Assumed surface area/mass" does not change but the actual specific surface area which is the "Actual surface area/mass" increases.

The titanium phosphate powder obtained by the method of this embodiment is suitable as additives to be added to cosmetic materials, such as sunscreen cosmetic materials, or pigments to be added to paints. The titanium phosphate powder obtained by the method of this embodiment is also suitable as white pigments for cosmetic materials.

The titanium phosphate plate-shaped particles used in the first step of the method of this embodiment can be manufactured by the method described in PTL 1, i.e., a method including reacting a raw material containing titanium and phosphorus by a hydrothermal synthesis method. As the raw material used in the hydrothermal synthesis method, a mixture of titanium sulfate (IV) (Ti $(SO_4)_2$) or titanyl sulfate ($TiOSO_4$) and phosphoric acid ($H_3PO_4$) is usable. The reaction conditions and the like of the hydrothermal synthesis method are described in detail in PTL 1.

Second Embodiment

A powder of this embodiment is a powder containing plate-shaped particles derived from titanium phosphate containing any of a "compound derived from titanium phosphate in which hydrogen of the titanium phosphate is replaced with alkali metal" or a "compound derived from titanium phosphate in which alkali metal is contained in crystals of the titanium phosphate". The ratio of the "actual specific surface area which is the specific surface area of the plate-shaped particles derived from titanium phosphate measured by a gas adsorption method" to the "assumed specific surface area which is the specific surface area measured by assuming the outer surface as a plane from the average particle size and the average thickness of the plate-shaped particles derived from titanium phosphate obtained by microscopic observation" (Actual specific surface area/Assumed specific surface area) is 1.5 or more.

The plate-shaped particles derived from titanium phosphate constituting the powder of this embodiment has an average thickness of 0.01 μm or more and 4 μm or less, an average primary particle diameter of 0.05 μm or more and 20 μm or less, and an aspect ratio (value obtained by dividing the average primary particle diameter by the average thickness) of 5 or more. The plate-shaped particles derived from titanium phosphate are hexagonal plate-shaped particles, and the assumed specific surface area is a value calculated by assuming the hexagonal plate-shaped particle as an ideal hexagonal column.

In the powder of this embodiment, due to the fact that the plate-shaped particles derived from titanium phosphate satisfy "Actual specific surface area/Assumed specific surface area≥1.5", the particles appropriately have surface irregularities and internal holes and the refreshing feeling when used as a powder for cosmetic materials is more excellent than that of a powder containing titanium phosphate plate-shaped particles with "Actual specific surface area/Assumed specific surface area<1.5".

Hence, the powder of this embodiment is suitable as white pigments for cosmetic materials. Further, the powder of this embodiment is also suitable as additives to be added to cosmetic materials, such as sunscreen cosmetic materials, or pigments to be added to paints.

The powder of this embodiment can be manufactured by the following method.

This manufacturing method includes a first step of obtaining a liquid in a state where the powder containing titanium phosphate plate-shaped particles is dispersed in an aqueous alkaline solution and having a pH around neutrality (dispersion liquid of the plate-shaped particles derived from titanium phosphate), a second step of separating the plate-shaped particles derived from titanium phosphate from the liquid, and a third step of drying the separated plate-shaped particles derived from titanium phosphate.

In the first step, the powder containing titanium phosphate plate-shaped particles is first dispersed in the aqueous alkaline solution. As methods therefor, the following four methods are mentioned, for example.

A first method is a method in which the aqueous alkaline solution is added to or a compound exhibiting alkalinity when melted in water is added to and mixed with a dispersion liquid in which the powder containing titanium phosphate plate-shaped particles is dispersed in water (hereinafter, also referred to as "titanium phosphate dispersion liquid"). A second method is a method including placing the powder containing titanium phosphate plate-shaped particles in a vessel, and then adding the aqueous alkaline solution to the vessel, followed by mixing.

A third method is a method in which the dispersion liquid in which the powder containing titanium phosphate plate-shaped particles is dispersed in water is added to or the powder containing titanium phosphate plate-shaped particles is added to and mixed with the aqueous alkaline solution. A fourth method is a method including placing a compound exhibiting alkalinity when melted in water in a vessel, and then placing the dispersion liquid in which the powder containing titanium phosphate plate-shaped particles is dispersed in water in the vessel, followed by mixing.

As the titanium phosphate plate-shaped particles, particles are used which are hexagonal plate-shaped particles and have an average thickness of 0.01 μm or more and 4 μm or less, an average primary particle diameter of 0.05 μm or more and 20 μm or less, and an aspect ratio, which is a value obtained by dividing the average primary particle diameter by the average thickness, of 5 or more.

As the aqueous alkaline solution, an aqueous sodium hydroxide solution, an aqueous potassium hydroxide solution, an aqueous sodium carbonate solution, and an aqueous potassium carbonate solution are used, for example. As the compound exhibiting alkalinity when melted in water, sodium carbonate or potassium carbonate is used, for example.

In the first step, protons of titanium phosphate are replaced with alkali metal ions to cause a neutralization reaction. With the progress of this neutralization reaction, the pH of the aqueous alkaline solution decreases or the pH of the titanium phosphate dispersion liquid increases. When the neutralization reaction is completed, the pH reaches a stabilized value around neutrality (for example, 5 or more and 9 or less). The mixing is continued until this state is reached or the mixture is left to stand after the mixing. The standing time when the mixture is left to stand after the mixing changes depending on the atmospheric temperature, but is suitably about 2 hours in the case of room temperature (25° C.)

In the first step, the titanium phosphate compound is changed to the "compound derived from titanium phosphate in which hydrogen of the titanium phosphate is replaced with alkali metal" or the "compound derived from titanium phosphate in which alkali metal is contained in crystals of the titanium phosphate".

In the first step, due to the formation of irregularities on the surface of the plate-shaped particles, the specific surface area of the plate-shaped particles increases, while the particle size remains unchanged. This specific surface area is not a specific surface area measured by assuming the surface of the plate-shaped particles as a plane (assumed specific surface area), but a specific surface area measured as a value including the area of surfaces formed by surface irregularities or internal holes (actual specific surface area).

In the second step, centrifugation or suction filtration, for example, is performed to separate the plate-shaped particles derived from titanium phosphate (in which the specific surface area is increased as compared with that of the titanium phosphate plate-shaped particles) obtained in the first step and water from each other.

In the third step, the separated particles are dried until a powder state is reached. The drying time changes depending on the drying temperature and is suitably about 1 day in the case of 105° C.

According to this manufacturing method, the particle size and the thickness of the hexagonal plate-shaped particles do not change by the treatment performed in the first step, and therefore the assumed surface area (for example, surface area calculated as a value obtained by assuming the crystal particle as an ideal hexagonal column and totalizing the areas of the eight surfaces constituting the hexagonal column based on the particle size and the thickness by image analysis of micrographs) does not change before and after the first step. However, the actual surface area (total value of the areas of all surfaces including surfaces of the surface irregularities and the internal holes of the hexagonal plate-shaped particles) increases after the first step. Also with respect to the specific surface area which is the surface area per unit mass, the assumed specific surface area which is the "Assumed surface area/mass" does not change but the actual specific surface area which is the "Actual surface area/mass" increases. Therefore, the ratio (Actual specific surface area/Assumed specific surface area)" can be set to 1.5 or more.

The titanium phosphate plate-shaped particles used in the first step of this manufacturing method can be manufactured by the method described in PTL 1, i.e., the method including reacting a raw material containing titanium and phosphorus by a hydrothermal synthesis method. As the raw material used in the hydrothermal synthesis method, a mixture of titanium sulfate (IV) (Ti (SO$_4$)$_2$) or titanyl sulfate (TiOSO$_4$) and phosphoric acid (H$_3$PO$_4$) is usable. The reaction conditions and the like of the hydrothermal synthesis method are described in detail in PTL 1.

Third Embodiment

The powder of this embodiment is a powder containing plate-shaped particles derived from titanium phosphate containing any of a "compound derived from titanium phosphate in which hydrogen of the titanium phosphate is replaced with alkali metal" or a "compound derived from titanium phosphate in which alkali metal is contained in crystals of the titanium phosphate". The ratio of the average deviation of the friction coefficient (MMD) to the average friction coefficient (MIU) (MMD/MIU) is 0.011 or more.

The plate-shaped particles derived from titanium phosphate constituting the powder of this embodiment has an average thickness of 0.01 μm or more and 4 μm or less, an average primary particle diameter of 0.05 μm or more and 20 μm or less, and an aspect ratio (value obtained by dividing the average primary particle diameter by the average thickness) of 5 or more. The plate-shaped particles derived from titanium phosphate are hexagonal plate-shaped particles, and the assumed specific surface area is a value calculated by assuming the hexagonal plate-shaped particle as an ideal hexagonal column.

Due to the fact that the powder of this embodiment satisfies that "the ratio of the average deviation of the friction coefficient (MMD) to the average friction coefficient (MIU) (MMD/MIU) is 0.011 or more", both slipperiness and a refreshing feeling when used as a powder for cosmetic materials are achieved as compared with a powder in which "the ratio of the average deviation of the friction coefficient (MMD) to the average friction coefficient (MIU) (MMD/MIU) is less than 0.011". The MMD is preferably 0.01 or more for the refreshing feeling and the MIU is preferably 1.45 or less for the slipperiness.

Hence, the powder of this embodiment is suitable as white pigments for cosmetic materials. Further, the powder of this embodiment is also suitable as additives to be added to cosmetic materials, such as sunscreen cosmetic materials, or pigments to be added to paints.

The powder of this embodiment can be manufactured by the same method as the method for manufacturing the powder of the second embodiment described above.

EXAMPLES

The present invention is more specifically described by illustrating Examples below.

First Example: Examples of First Aspect

[Manufacturing of Titanium Phosphate Powder Containing Titanium Phosphate Hexagonal Plate-Shaped Particles (Sample No. 1-1)]

First, titanyl sulfate and phosphoric acid were reacted by a hydrothermal synthesis method, thereby manufacturing a titanium phosphate powder. The conditions of the hydrothermal synthesis were set as follows: the titanium concentration [Ti] of a raw material (mixture of titanyl sulfate and phosphoric acid) was set to 0.30 mol/L, the phosphorus concentration [P] was set to 3.22 mol/L, the concentration ratio thereof [P]/[Ti] was set to 11, the reaction temperature was set to 130° C., and the reaction time was set to 5 hours.

Specifically, first, titanyl sulfate as a titanium source and phosphoric acid as a phosphorus source were mixed, thereby obtaining a mixture. Next, the obtained mixture was placed in a reaction vessel (autoclave with a capacity of 1.4 L) and heated at 130° C. for 5 hours. At that time, the reaction vessel was not pressurized, and the pressure inside the vessel was set to a value naturally determined by the heating temperature (natural pressurization).

After 5 hours, a lid was opened to cool a slurry in the vessel to room temperature, the slurry was filtered, and then pure water was applied to a solid content remaining on a filter paper for cleaning. Next, pure water was added to the solid content after the cleaning to obtain a slurry, and 29% ammonium water (aqueous solution of ammonium salt) was added to the slurry until the pH reached 7. Next, the slurry was filtered, and then the same cleaning as above was performed to separate the solid content. The solid content was dried (left to stand at a temperature of 105° C. for 24 hours) to obtain a powder.

As a result of analyzing the powder of Sample No. 1-1 thus obtained using an X-ray diffractometer, it was able to be confirmed that the particles constituting the powder were crystalline titanium phosphate having a rational formula of $Ti(HPO_4)_2 \cdot H_2O$.

The whiteness of the powder of Sample No. 1-1 was 94.6 as measured with an ultraviolet-visible spectrophotometer "UV-2450" manufactured by Shimadzu Corporation under the conditions of a D65 illumination and a field of view of 2°. More specifically, the whiteness of the powder of Sample No. 1-1 was 94.6 as measured according to JIS Z 8715.

Figure 1B:
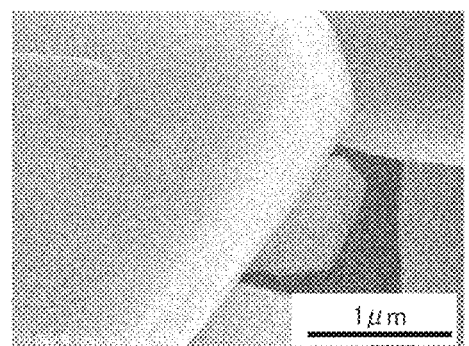

When the powder of Sample No. 1-1 was observed with a scanning electron microscope, it was able to be confirmed that the particles constituting the powder had a plate shape and contained a large number of hexagonal plate-shaped particles as illustrated in FIG. 1A. Further, irregularities were not able to be confirmed on the surface of the plate-shaped particles as illustrated in FIG. 1B. The average thickness of the crystal particles constituting the powder of Sample No. 1-1 was 0.44 μm as measured from an image of the scanning electron microscope.

The average primary particle diameter of the crystal particles constituting the powder of Sample No. 1-1 was 3.72 μm as measured by analyzing the image of the scanning electron microscope using image analysis software "Mac-View ver. 4" manufactured by MOUNTECH Co., Ltd. By the calculation using these measured values (3.72/0.44), the aspect ratio of the crystal particles constituting the powder of Sample No. 1-1 was 8.

Further, the assumed specific surface area was 2.22 m²/g as calculated by assuming the crystal particle as an ideal hexagonal column using these measured values.

Further, the actual specific surface area of the powder of Sample No. 1-1 was 2.83 m²/g as measured by the BET flow method (gas adsorption method) using a fully automatic specific surface area measuring device "Macsorb (registered trademark) HM-1210" of MOUNTECH Co., Ltd.

The refractive index of the powder of Sample No. 1-1 was 1.73 as measured by the following method.

First, the powder of Sample No. 1-1 and polymethyl methacrylate (film substrate: transparent resin serving as the base of the film) were placed in and mixed with N-methylpyrrolidone (solvent capable of dissolving the film substrate), and then the powder was dispersed to obtain a liquid in which the polymethyl methacrylate was dissolved. Two or more of the liquids were obtained by changing the content rate of the powder. Using these liquids, a 600 μm thick coating film was formed on a PET film and dried at 80° C., thereby forming a film containing only the powder and the resin. After cooling, the film was peeled from the PET film.

The refractive indices of the plurality of films thus obtained were measured using a refractometer "Prism Coupler Model 2010/M" manufactured by Metricon Corporation and a helium•neon laser light with a wavelength of 632.8 nm as a light source. The measured values of the refractive indices of the plurality of films were plotted on a graph with the content rate (vol %) of the powder on the horizontal axis and the refractive index on the vertical axis, and the plots were approximated by a straight line. A value of the refractive index at a point where this straight line was extrapolated to a point where the content rate of the powder reached 100% was defined as the refractive index of the powder.

The oil absorption per 100 g of the powder of Sample No. 1-1 was 57 ml/100 g as measured by a method according to JIS K 5101-13.

The MIU (average friction coefficient) was measured as the friction coefficient of the powder of Sample No. 1-1 using a friction tester "KES-SE" of KATO TECH CO., LTD. In the measurement, a double-sided tape was stuck onto a glass plate of a measuring table, and the powder was placed and fixed thereon. A 10 mm square silicon sensor was placed on this powder and moved under the conditions of a static load of 25 g and a scanning speed of 1 mm/sec, and then the MIU was measured within the range of 20 mm. As a result, the MIU was 0.98.

[Implementation of Method for Increasing Specific Surface Area of Titanium Phosphate Plate-Shaped Particles (Samples No. 1-2, No. 1-3)]

Next, the following treatment (treatment with an aqueous alkaline solution, separation, drying) was applied to the powder of Sample No. 1-1, thereby implementing the "method for increasing the specific surface area of titanium phosphate plate-shaped particles" described in the embodiments.

<Sample No. 1-2>

4 g of the powder of Sample No. 1-1 was placed in and mixed with 36 g of pure water, thereby obtaining a dispersion liquid of titanium phosphate plate-shaped particles. 2.60 g of an aqueous 48% sodium hydroxide solution was added to this dispersion liquid, mixed for 5 minutes, and then left to stand at room temperature (25° C.) for 2 hours. Next, suction filtration was performed to separate the solid content. The separated solid content was dried at 105° C. for 1 day. Thus, a powder of Sample No. 1-2 was obtained.

The powder of Sample No. 1-2 was also measured for the physical properties by the same methods as those for the powder of Sample No. 1-1.

As a result of analyzing the powder of Sample No. 1-2 thus obtained using an X-ray diffractometer, it was found that the particles constituting the powder were crystalline sodium titanium phosphate having a rational formula of $Na_2Ti(PO_4)_2 \cdot H_2O$. When this powder was subjected to elemental analysis using an energy dispersive x-ray analysis (EDX) device, the presence of a sodium element (Na) was confirmed. More specifically, this powder is a powder containing "plate-shaped particles derived from titanium phosphate containing a compound derived from titanium phosphate in which hydrogen of the titanium phosphate is replaced with alkali metal".

Figure 2A:
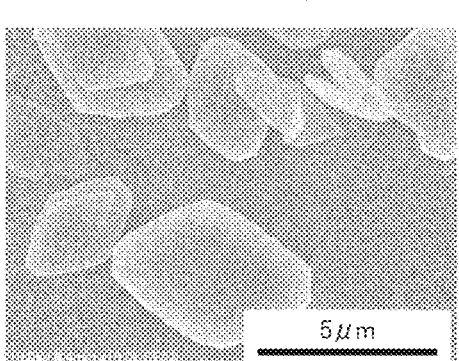
FIGS. 2A and 2B are SEM images of plate-shaped particles constituting powders of Samples No. 1-2, No. 4-2, No. 5-2 obtained in Examples.
Figure 2B:
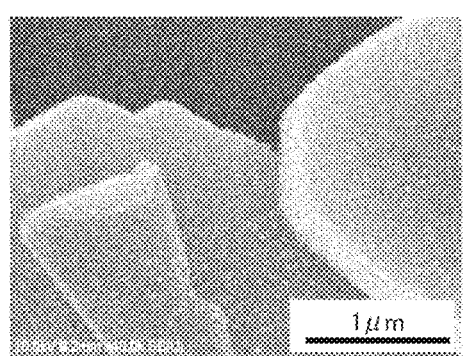

When the powder of Sample No. 1-2 was observed with a scanning electron microscope, it was able to be confirmed that the particles constituting the powder had a plate shape and contained a large number of hexagonal plate-shaped particles as illustrated in FIG. 2A. Further, the formation of irregularities on the surface of the plate-shaped particles was also able to be confirmed as illustrated in FIG. 2B.

<Sample No. 1-3>

4 g of the powder of Sample No. 1-1 was placed in and mixed with 36 g of pure water, thereby obtaining a dispersion liquid of titanium phosphate plate-shaped particles. 3.65 g of an aqueous 48% potassium hydroxide solution was added to this dispersion liquid, mixed for 5 minutes, and then left to stand at room temperature (25° C.) for 2 hours. Next, suction filtration was performed to separate the solid content. The separated solid content was dried at 105° C. for 1 day. Thus, a powder of Sample No. 1-3 was obtained.

As a result of analyzing the powder of Sample No. 1-3 thus obtained using an X-ray diffractometer, it was found that the particles constituting the powder were almost the same as the crystalline titanium phosphate having the rational formula of Ti(HPO$_4$)$_2$·H$_2$O. When this powder was subjected to elemental analysis using an energy dispersive x-ray analysis (EDX) device, the presence of a potassium element (K) was confirmed. More specifically, this powder is a powder containing "plate-shaped particles derived from titanium phosphate containing a compound derived from titanium phosphate in which alkali metal is contained in crystals of the titanium phosphate".

The powder of Sample No. 1-3 was also measured for the physical properties by the same methods as those for the powder of Sample No. 1-1.

Figure 3A:
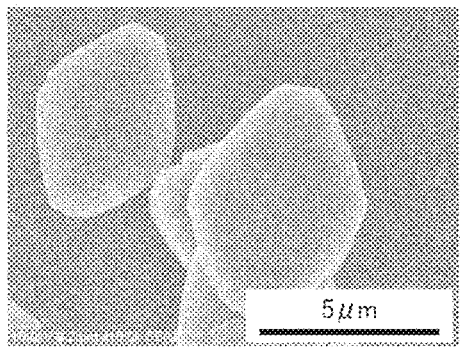
FIGS. 3A and 3B are SEM images of plate-shaped particles constituting powders of Samples No. 1-3, No. 4-3, No. 5-3 obtained in Examples.
Figure 3B:
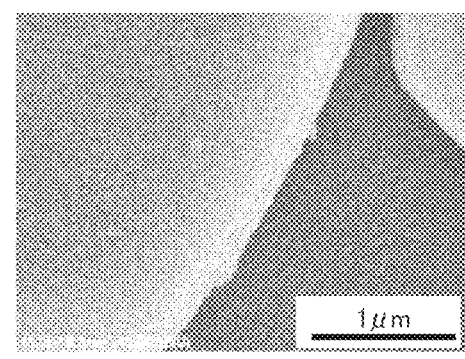

When the powder of Sample No. 1-3 was observed with a scanning electron microscope, it was able to be confirmed that the particles constituting the powder had a plate shape and contained a large number of hexagonal plate-shaped particles as illustrated in FIG. 3A. Further, the formation of irregularities on the surface of the plate-shaped particles was also able to be confirmed as illustrated in FIG. 3B.

The values of the physical properties obtained for Samples No. 1-1 to No. 1-3 are shown in Table 1.

phosphoric acid) was set to 0.30 mol/L, the phosphorus concentration [P] was set to 3.22 mol/L, the concentration ratio thereof [P]/[Ti] was set to 11, the reaction temperature was set to 130° C., and the reaction time was set to 3 hours.

Specifically, first, titanyl sulfate as a titanium source and phosphoric acid as a phosphorus source were mixed, thereby obtaining a mixture. Next, the obtained mixture was placed in a reaction vessel (autoclave with a capacity of 200 L) and heated at 130° C. for 3 hours. At that time, the reaction vessel was not pressurized, and the pressure inside the vessel was set to a value naturally determined by the heating temperature (natural pressurization).

After 3 hours, a lid was opened to cool a slurry in the vessel to room temperature, the slurry was filtered, and then pure water was applied to a solid content remaining on a filter paper for cleaning. Next, pure water was added to the solid content after the cleaning to obtain a slurry, and 29% ammonium water (aqueous solution of ammonium salt) was added to the slurry until the pH reached 7. Next, the slurry was filtered, and then the same cleaning as above was

TABLE 1

| No. | Type of aqueous alkaline solution | pH | Whiteness | Average thickness (μm) | Average primary particle size (μm) | Aspect ratio | Refractive index | Oil absorption (ml/100 g) | Specific surface area (m²/g) Assumed | Actual | MIU |
|---|---|---|---|---|---|---|---|---|---|---|---|
| 1-1 | — | 3.6 | 94.6 | 0.44 | 3.72 | 8 | 1.73 | 57 | 2.22 | 2.83 | 0.98 |
| 1-2 | NaOH | 6.9 | 94.9 | 0.47 | 3.74 | 8 | 1.79 | 57 | 2.11 | 14.1 | 0.93 |
| 1-3 | KOH | 6.5 | 95.7 | 0.48 | 3.71 | 8 | 1.76 | 77 | 2.08 | 51.1 | 0.90 |

As is understood from Table 1, the actual specific surface area is significantly increased and the pH is higher in the plate-shaped particles derived from titanium phosphate (No. 1-2, No. 1-3) obtained by the treatment with the aqueous alkaline solution than in the titanium phosphate plate-shaped particles before the treatment with the aqueous alkaline solution (No. 1-1), but the other physical properties are almost unchanged.

More specifically, according to the "method including a treatment step using an aqueous alkaline solution" described above applied to the powder of Sample No. 1-1, it is found that the specific surface area (actual surface area) can be increased without changing the particle size of the titanium phosphate plate-shaped particles.

The powders of Samples No. 1-2 and No. 1-3 are not significantly different from the powder of Sample No. 1-1 in the whiteness, the average thickness, the average primary particle size, the aspect ratio, the refractive index, the assumed specific surface area, and the MIU and have values suitable as a powder for cosmetic materials.

The powders of Samples No. 1-2 and No. 1-3 are neutral, whereas the powder of Sample No. 1-1 is acidic, and have properties (skin-friendly properties) preferable as a powder for cosmetic materials.

Second Example: Examples of First Aspect

[Manufacturing of Titanium Phosphate Powder Containing Titanium Phosphate Hexagonal Plate-Shaped Particles (Sample No. 2-1)]

First, titanyl sulfate and phosphoric acid were reacted by a hydrothermal synthesis method, thereby manufacturing a titanium phosphate powder. The conditions of the hydrothermal synthesis were set as follows: the titanium concentration [Ti] of a raw material (mixture of titanyl sulfate and performed to separate the solid content. The solid content was dried (left to stand at a temperature of 105° C. for 24 hours) to obtain a powder.

As a result of analyzing the powder of Sample No. 2-1 thus obtained using an X-ray diffractometer, it was able to be confirmed that the particles constituting the powder were crystalline titanium phosphate having the rational formula of Ti(HPO$_4$)$_2$·H$_2$O.

The powder of Sample No. 2-1 was also measured for the physical properties by the same methods as those for the powder of Sample No. 1-1.

Figure 4A:
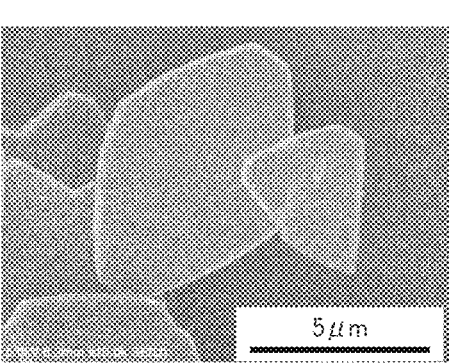
FIGS. 4A and 4B are SEM images of plate-shaped particles constituting powders of Samples No. 2-1, No. 4-4, No. 5-4 obtained in Examples.
Figure 4B:
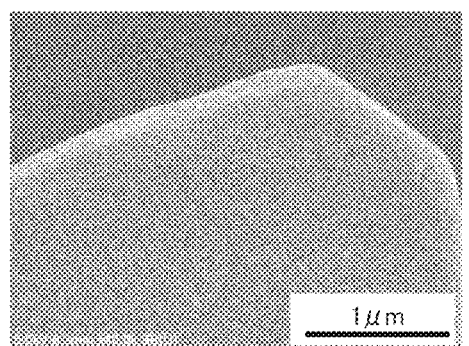

When the powder of Sample No. 2-1 was observed with a scanning electron microscope, it was able to be confirmed that the particles constituting the powder had a plate shape and contained a large number of hexagonal plate-shaped particles as illustrated in FIG. 4A. Further, irregularities were not able to be confirmed on the surface of the plate-shaped particles as illustrated in FIG. 4B.

[Implementation of Method for Increasing Specific Surface Area of Titanium Phosphate Plate-Shaped Particles (Samples No. 2-2, No. 2-3, No. 2-4, No. 2-5)]

Next, the following treatment (treatment with an aqueous alkaline solution, separation, drying) was applied to the powder of Sample No. 2-1, thereby implementing the "method for increasing the specific surface area of titanium phosphate plate-shaped particles" described in the embodiments.

<Sample No. 2-2>

4 g of the powder of Sample No. 2-1 was placed in and mixed with 36 g of pure water, thereby obtaining a dispersion liquid of titanium phosphate plate-shaped particles. 2.60 g of an aqueous 48% sodium hydroxide solution was added to this dispersion liquid, mixed for 5 minutes, and then left to stand at room temperature (25° C.) for 2 hours. Next, suction filtration was performed to separate the solid content. The separated solid content was dried at 105° C. for 1 day. Thus, a powder of Sample No. 2-2 was obtained.

As a result of analyzing the powder of Sample No. 2-2 thus obtained using an X-ray diffractometer, it was found that the particles constituting the powder were crystalline sodium titanium phosphate having the rational formula of $Na_2Ti(PO_4)_2 \cdot H_2O$. When this powder was subjected to elemental analysis using an energy dispersive x-ray analysis (EDX) device, the presence of a sodium element (Na) was confirmed. More specifically, this powder is a powder containing the "plate-shaped particles derived from titanium phosphate containing a compound derived from titanium phosphate in which hydrogen of the titanium phosphate is replaced with alkali metal".

The powder of Sample No. 2-2 was also measured for the physical properties by the same methods as those for the powder of Sample No. 1-1.

Figure 5A:
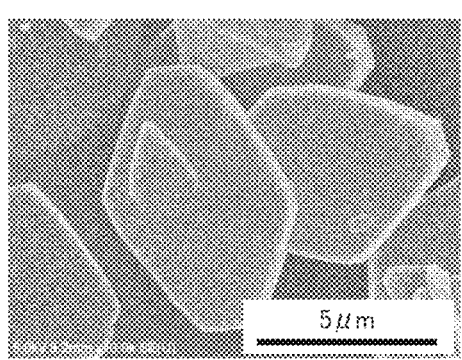
FIGS. 5A and 5B are SEM images of plate-shaped particles constituting powders of Samples No. 2-2, No. 4-5 obtained in Examples.
Figure 5B:
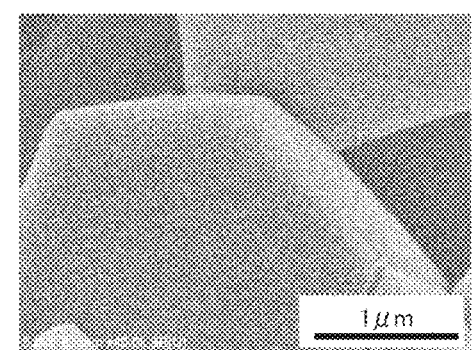

When the powder of Sample No. 2-2 was observed with a scanning electron microscope, it was able to be confirmed that the particles constituting the powder had a plate shape and contained a large number of hexagonal plate-shaped particles as illustrated in FIG. 5A. Further, the formation of irregularities on the surface of the plate-shaped particles was also able to be confirmed as illustrated in FIG. 5B.

<Sample No. 2-3>

4 g of the powder of Sample No. 2-1 was placed in and mixed with 36 g of pure water, thereby obtaining a dispersion liquid of titanium phosphate plate-shaped particles. 3.65 g of an aqueous 48% potassium hydroxide solution was added to this dispersion liquid, mixed for 5 minutes, and then left to stand at room temperature (25° C.) for 2 hours. Next, suction filtration was performed to separate the solid content. The separated solid content was dried at 105° C. for 1 day. Thus, a powder of Sample No. 2-3 was obtained.

As a result of analyzing the powder of Sample No. 2-3 thus obtained using an X-ray diffractometer, it was found that the particles constituting the powder were almost the same as the crystalline titanium phosphate having the rational formula of $Ti(HPO_4)_2 \cdot H_2O$. When this powder was subjected to elemental analysis using an energy dispersive x-ray analysis (EDX) device, the presence of a potassium element (K) was confirmed. More specifically, this powder is a powder containing the "plate-shaped particles derived from titanium phosphate containing a compound derived from titanium phosphate in which alkali metal is contained in crystals of the titanium phosphate".

The powder of Sample No. 2-3 was also measured for the physical properties by the same methods as those for the powder of Sample No. 1-1.

Figure 6A:
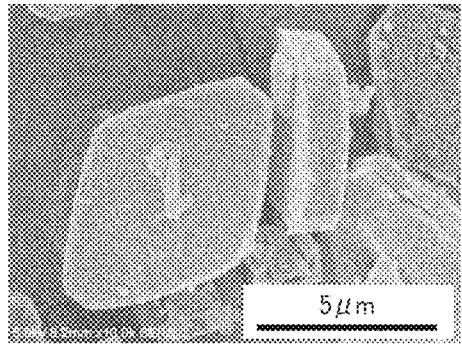
FIGS. 6A and 6B are SEM images of plate-shaped particles constituting powders of Samples No. 2-3, No. 4-6, No. 5-5 obtained in Examples.
Figure 6B:
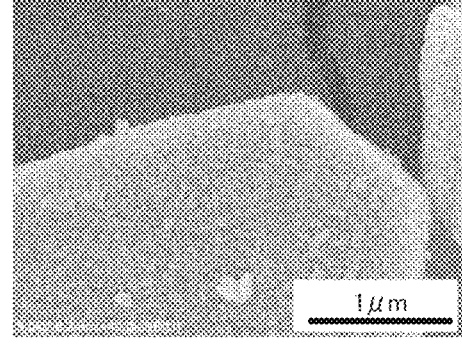

When the powder of Sample No. 2-3 was observed with a scanning electron microscope, it was able to be confirmed that the particles constituting the powder had a plate shape and contained a large number of hexagonal plate-shaped particles as illustrated in FIG. 6A. Further, the formation of irregularities on the surface of the plate-shaped particles was also able to be confirmed as illustrated in FIG. 6B.

<Sample No. 2-4>

4 g of the powder of Sample No. 2-1 was placed in and mixed with 36 g of pure water, thereby obtaining a dispersion liquid of titanium phosphate plate-shaped particles. 1.65 g of a sodium carbonate powder was added to this dispersion liquid, mixed for 5 minutes, and then left to stand at room temperature (25° C.) for 2 hours. Next, suction filtration was performed to separate the solid content. The separated solid content was dried at 105° C. for 1 day. Thus, a powder of Sample No. 2-4 was obtained.

As a result of analyzing the powder of Sample No. 2-4 thus obtained using an X-ray diffractometer, it was found that the particles constituting the powder were crystalline sodium titanium phosphate having the rational formula of $Na_2Ti(PO_4)_2 \cdot H_2O$. When this powder was subjected to elemental analysis using an energy dispersive x-ray analysis (EDX) device, the presence of a sodium element (Na) was confirmed. More specifically, this powder is a powder containing the "plate-shaped particles derived from titanium phosphate containing a compound derived from titanium phosphate in which hydrogen of the titanium phosphate is replaced with alkali metal".

The powder of Sample No. 2-4 was also measured for the physical properties by the same methods as those for the powder of Sample No. 1-1.

Figure 7A:
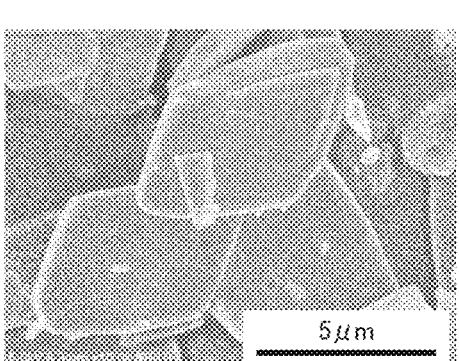
FIGS. 7A and 7B are SEM images of plate-shaped particles constituting powders of Samples No. 2-4, No. 4-7, No. 5-6 obtained in Examples.
Figure 7B:
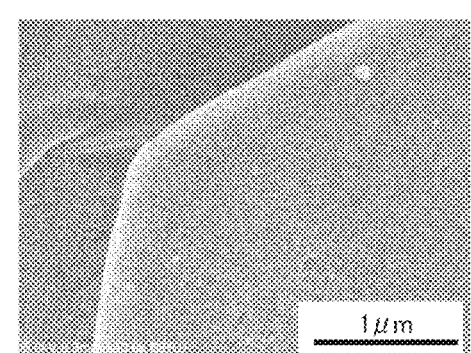

When the powder of Sample No. 2-4 was observed with a scanning electron microscope, it was able to be confirmed that the particles constituting the powder had a plate shape and contained a large number of hexagonal plate-shaped particles as illustrated in FIG. 7A. Further, the formation of irregularities on the surface of the plate-shaped particles was also able to be confirmed as illustrated in FIG. 7B.

<Sample No. 2-5>

4 g of the powder of Sample No. 2-1 was placed in and mixed with 36 g of pure water, thereby obtaining a dispersion liquid of titanium phosphate plate-shaped particles. 2.16 g of a potassium carbonate powder was added to this dispersion liquid, mixed for 5 minutes, and then left to stand at room temperature (25° C.) for 2 hours. Next, suction filtration was performed to separate the solid content. The separated solid content was dried at 105° C. for 1 day. Thus, a powder of Sample No. 2-5 was obtained.

As a result of analyzing the powder of Sample No. 2-5 thus obtained using an X-ray diffractometer, it was found that the particles constituting the powder were almost the same as the crystalline titanium phosphate having the rational formula of $Ti(HPO_4)_2 \cdot H_2O$. When this powder was subjected to elemental analysis using an energy dispersive x-ray analysis (EDX) device, the presence of a potassium element (K) was confirmed. More specifically, this powder is a powder containing the "plate-shaped particles derived from titanium phosphate containing a compound derived from titanium phosphate in which alkali metal is contained in crystals of the titanium phosphate".

The powder of Sample No. 2-5 was also measured for the physical properties by the same methods as those for the powder of Sample No. 1-1.

Figure 8A:
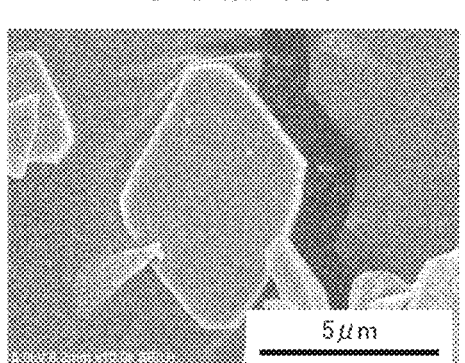
FIGS. 8A and 8B are SEM images of plate-shaped particles constituting powders of Samples No. 2-5, No. 4-8 obtained in Examples.
Figure 8B:
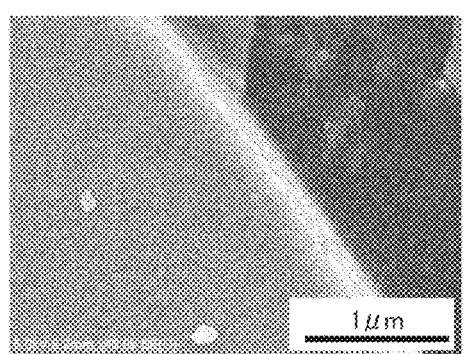

When the powder of Sample No. 2-5 was observed with a scanning electron microscope, it was able to be confirmed that the particles constituting the powder had a plate shape and contained a large number of hexagonal plate-shaped particles as illustrated in FIG. 8A. Further, the formation of irregularities on the surface of the plate-shaped particles was also able to be confirmed as illustrated in FIG. 8B.

These values are shown in Table 2. Although the refractive indices of the powders of Samples No. 2-1 to No. 2-5 were not measured, it can be presumed that the values are almost the same as the refractive indices of the powders of Samples No. 1-1 to No. 1-3.

TABLE 2

| No. | Type of aqueous alkaline solution | pH | Whiteness | Average thickness (μm) | Average primary particle size (μm) | Aspect ratio | Refractive index | Oil absorption (ml/100 g) | Specific surface area (m²/g) Assumed | Actual | MIU |
|---|---|---|---|---|---|---|---|---|---|---|---|
| 2-1 | — | 3.7 | 98.4 | 0.77 | 6.97 | 9 | — | 47 | 1.26 | 1.67 | 0.92 |
| 2-2 | NaOH | 7.1 | 97.1 | 0.80 | 6.95 | 9 | — | 46 | 1.22 | 10.1 | 0.95 |
| 2-3 | KOH | 7.0 | 96.4 | 0.80 | 6.95 | 9 | — | 56 | 1.22 | 24.0 | 0.89 |
| 2-4 | $Na_2CO_3$ | 5.6 | 98.0 | 0.79 | 6.98 | 9 | — | 47 | 1.23 | 3.24 | 0.94 |
| 2-5 | $K_2CO_3$ | 5.9 | 95.0 | 0.80 | 6.95 | 9 | — | 50 | 1.22 | 4.44 | 0.83 |

As is understood from Table 2, the actual specific surface area is significantly increased and the pH is higher in the titanium phosphate plate-shaped particles after the treatment with the aqueous alkaline solution (No. 2-2 to No. 2-5) than in the titanium phosphate plate-shaped particles before the treatment (No. 2-1), but the other physical properties are almost unchanged.

More specifically, according to the "method including a treatment step using an aqueous alkaline solution" described above applied to the powder of Sample No. 2-1, it is found that the specific surface area (actual surface area) can be increased without changing the particle size of the titanium phosphate plate-shaped particles.

The powders of Samples No. 2-2 to No. 2-5 are not significantly different from the powder of Sample No. 2-1 in the whiteness, the average thickness, the average primary particle size, the aspect ratio, the assumed specific surface area, and the MIU and have values suitable as a powder for cosmetic materials.

The powders of Samples No. 2-2 to No. 2-5 are neutral, whereas the powder of Sample No. 2-1 is acidic, and have properties (skin-friendly properties) preferable as a powder for cosmetic materials.

Third Example: Examples of First Aspect

[Manufacturing of Titanium Phosphate Powder Containing Titanium Phosphate Hexagonal Plate-Shaped Particles (Sample No. 3-1)]

First, titanyl sulfate and phosphoric acid were reacted by a hydrothermal synthesis method, thereby manufacturing a titanium phosphate powder. The conditions of the hydrothermal synthesis were set as follows: the titanium concentration [Ti] of a raw material (mixture of titanyl sulfate and phosphoric acid) was set to 0.30 mol/L, the phosphorus concentration [P] was set to 3.93 mol/L, the concentration ratio thereof [P]/[Ti] was set to 13, the reaction temperature was set to 90° C., and the reaction time was set to 5 hours.

Specifically, first, titanyl sulfate as a titanium source and phosphoric acid as a phosphorus source were mixed, thereby obtaining a mixture. Next, the obtained mixture was placed in a reaction vessel (autoclave with a capacity of 1.4 L) and heated at 90° C. for 5 hours. At that time, the reaction vessel was not pressurized, and the pressure inside the vessel was set to a value naturally determined by the heating temperature (natural pressurization).

After 5 hours, a lid was opened to cool a slurry in the vessel to room temperature, the slurry was filtered, and then pure water was applied to a solid content remaining on a filter paper for cleaning. Next, pure water was added to the solid content after the cleaning to obtain a slurry, and 29% ammonium water (aqueous solution of ammonium salt) was added to the slurry until the pH reached 7. Next, the slurry was filtered, and then the same cleaning as above was performed to separate the solid content. The solid content was dried (left to stand at a temperature of 105° C. for 24 hours) to obtain a powder.

As a result of analyzing the powder of Sample No. 3-1 thus obtained using an X-ray diffractometer, it was able to be confirmed that the particles constituting the powder were crystalline titanium phosphate having the rational formula of $Ti(HPO_4)_2 \cdot H_2O$.

The powder of Sample No. 3-1 was also measured for the physical properties by the same methods as those for the powder of Sample No. 1-1.

Figure 9:
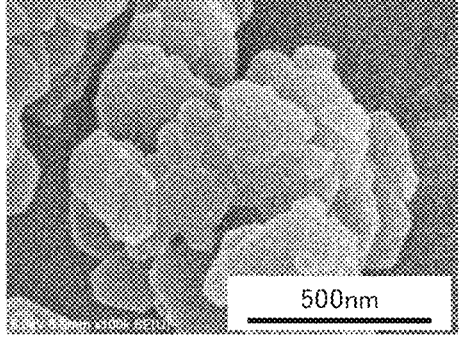
FIG. 9 is a SEM image of plate-shaped particles constituting powders of Samples No. 3-1, No. 4-9 obtained in Examples.

When the powder of Sample No. 3-1 was observed with a scanning electron microscope, it was able to be confirmed that the particles constituting the powder had a plate shape and contained a large number of hexagonal plate-shaped particles as illustrated in FIG. 9. Further, irregularities were not able to be confirmed on the surface of the plate-shaped particles.

[Implementation of Method for Increasing Specific Surface Area of Titanium Phosphate Plate-Shaped Particles (Sample No. 3-2)]

Next, the following treatment (treatment with an aqueous alkaline solution, separation, drying) was applied to the powder of Sample No. 3-1, thereby implementing the "method for increasing the specific surface area of titanium phosphate plate-shaped particles" described in the embodiments.

<Sample No. 3-2>

4 g of the powder of Sample No. 3-1 was placed in and mixed with 36 g of pure water, thereby obtaining a dispersion liquid of titanium phosphate plate-shaped particles. 2.60 g of an aqueous 48% sodium hydroxide solution was added to this dispersion liquid, mixed for 5 minutes, and then left to stand at room temperature (25° C.) for 2 hours. Next, suction filtration was performed to separate the solid content. The separated solid content was dried at 105° C. for 1 day. Thus, a powder of Sample No. 3-2 was obtained.

As a result of analyzing the powder of Sample No. 3-2 thus obtained using an X-ray diffractometer, it was found that the particles constituting the powder were crystalline sodium titanium phosphate having the rational formula of $Na_2Ti(PO_4)_2 \cdot H_2O$. When this powder was subjected to elemental analysis using an energy dispersive x-ray analysis (EDX) device, the presence of a sodium element (Na) was confirmed. More specifically, this powder is a powder containing the "plate-shaped particles derived from titanium phosphate containing a compound derived from titanium phosphate in which hydrogen of the titanium phosphate is replaced with alkali metal".

The powder of Sample No. 3-2 was also measured for the physical properties by the same methods as those for the powder of Sample No. 1-1.

Figure 10:
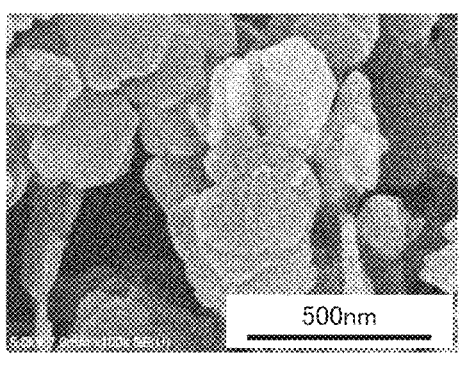
FIG. 10 is a SEM image of plate-shaped particles constituting powders of Samples No. 3-2, No. 4-10 obtained in Examples.

When the powder of Sample No. 3-2 was observed with a scanning electron microscope, it was able to be confirmed that the particles constituting the powder had a plate shape and contained a large number of hexagonal plate-shaped particles as illustrated in FIG. 10. Further, the formation of irregularities on the surface of the plate-shaped particles was also able to be confirmed.

These values are shown in Table 3. Although the refractive indices of the powders of Samples No. 3-1, No. 3-2 were not measured, it can be presumed that the values are almost the same as the refractive indices of the powders of Samples No. 1-1 to No. 1-3.

filter paper for cleaning. Next, pure water was added to the solid content after the cleaning to obtain a slurry, and 29% ammonium water (aqueous solution of ammonium salt) was added to the slurry until the pH reached 7. Next, the slurry was filtered, and then the same cleaning as above was performed to separate the solid content. The solid content was dried (left to stand at a temperature of 105° C. for 24 hours) to obtain a powder.

As a result of analyzing the powder of Sample No. 4-1 thus obtained using an X-ray diffractometer, it was able to be

TABLE 3

| No. | Type of aqueous alkaline solution | pH | Whiteness | Average thickness (μm) | Average primary particle size (μm) | Aspect ratio | Refractive index | Oil absorption (ml/100 g) | Specific surface area (m$^2$/g) Assumed | Specific surface area (m$^2$/g) Actual |
|---|---|---|---|---|---|---|---|---|---|---|
| 3-1 | — | 2.3 | 96.9 | 0.029 | 0.25 | 9 | — | 100 | 33.8 | 31.4 |
| 3-2 | NaOH | 6.8 | 99.5 | 0.031 | 0.23 | 7 | — | 97 | 32.7 | 51.5 |

As is understood from Table 3, the actual specific surface area is significantly increased and the pH is higher in the titanium phosphate plate-shaped particles after the treatment with the aqueous alkaline solution (No. 3-2) than in the titanium phosphate plate-shaped particles before the treatment (No. 3-1), but the other physical properties are almost unchanged.

More specifically, according to the "method including a treatment step using an aqueous alkaline solution" described above applied to the powder of Sample No. 3-1, it is found that the specific surface area (actual surface area) can be increased without changing the particle size of the titanium phosphate plate-shaped particles.

The powder of Sample No. 3-2 is not significantly different from the powder of Sample No. 3-1 in the whiteness, the average thickness, the average primary particle size, the aspect ratio, and the assumed specific surface area and has values suitable as a powder for cosmetic materials.

The powder of Sample No. 3-2 is neutral, whereas the powder of Sample No. 3-1 is acidic, and has properties (skin-friendly properties) preferable as a powder for cosmetic materials.

Fourth Example: Examples of Second Aspect

<Sample No. 4-1>

First, titanyl sulfate and phosphoric acid were reacted by a hydrothermal synthesis method, thereby manufacturing a titanium phosphate powder. The conditions of the hydrothermal synthesis were set as follows: the titanium concentration [Ti] of a raw material (mixture of titanyl sulfate and phosphoric acid) was set to 0.30 mol/L, the phosphorus concentration [P] was set to 3.22 mol/L, the concentration ratio thereof [P]/[Ti] was set to 11, the reaction temperature was set to 130° C., and the reaction time was set to 5 hours.

Specifically, first, titanyl sulfate as a titanium source and phosphoric acid as a phosphorus source were mixed, thereby obtaining a mixture. Next, the obtained mixture was placed in a reaction vessel (autoclave with a capacity of 1.4 L) and heated at 130° C. for 5 hours. At that time, the reaction vessel was not pressurized, and the pressure inside the vessel was set to a value naturally determined by the heating temperature (natural pressurization).

After 5 hours, a lid was opened to cool a slurry in the vessel to room temperature, the slurry was filtered, and then pure water was applied to a solid content remaining on a confirmed that the particles constituting the powder were crystalline titanium phosphate having the rational formula of Ti(HPO$_4$)$_2$·H$_2$O. More specifically, this powder is neither a powder containing the "plate-shaped particles derived from titanium phosphate containing a compound derived from titanium phosphate in which hydrogen of the titanium phosphate is replaced with alkali metal" nor a powder containing the "plate-shaped particles derived from titanium phosphate containing a compound derived from titanium phosphate in which alkali metal is contained in crystals of the titanium phosphate".

The whiteness of the powder of Sample No. 4-1 was 94.6 as measured with an ultraviolet-visible spectrophotometer "UV-2450" manufactured by Shimadzu Corporation under the conditions of a D65 illumination and a field of view of 2°. More specifically, the whiteness of the powder of Sample No. 4-1 was 94.6 as measured according to JIS Z 8715.

When the powder of Sample No. 4-1 was observed with a scanning electron microscope, it was able to be confirmed that the particles constituting the powder had a plate shape and contained a large number of hexagonal plate-shaped particles as illustrated in FIG. 1A. Further, irregularities were not able to be confirmed on the surface of the plate-shaped particles as illustrated in FIG. 1B. The average thickness of the crystal particles constituting the powder of Sample No. 4-1 was 0.44 μm as measured from an image of the scanning electron microscope.

The average primary particle diameter of the crystal particles constituting the powder of Sample No. 4-1 was 3.72 μm as measured by analyzing the image of the scanning electron microscope using image analysis software "MacView ver. 4" manufactured by MOUNTECH Co., Ltd. By the calculation using these measured values (3.72/0.44), the aspect ratio of the crystal particles constituting the powder of Sample No. 4-1 was 8.

Further, the assumed specific surface area was 2.22 m$^2$/g as calculated by assuming the crystal particle as an ideal hexagonal column using these measured values. The actual specific surface area of the powder of Sample No. 4-1 was 2.83 m$^2$/g as measured by the BET flow method (gas adsorption method) using a fully automatic specific surface area measuring device "Macsorb (registered trademark) HM-1210" of MOUNTECH Co., Ltd. As a result, the value of "Actual specific surface area/Assumed specific surface area" was 1.27.

The refractive index of the powder of Sample No. 4-1 was 1.73 as measured by the following method.

First, the powder of Sample No. 4-1 and polymethyl methacrylate (film substrate: transparent resin serving as the base of the film) were placed in and mixed with N-methylpyrrolidone (solvent capable of dissolving the film substrate), and then the powder was dispersed to obtain a liquid in which the polymethyl methacrylate was dissolved. Two or more of the liquids were obtained by changing the content rate of the powder. Using these liquids, a 600 μm thick coating film was formed on a PET film and dried at 80° C., thereby forming a film containing only the powder and the resin. After cooling, the film was peeled from the PET film.

The refractive indices of the plurality of films thus obtained were measured using a refractometer "Prism Coupler Model 2010/M" manufactured by Metricon Corporation and a helium•neon laser light with a wavelength of 632.8 nm as a light source. The measured values of the refractive indices of the plurality of films were plotted on a graph with the content rate (vol %) of the powder on the horizontal axis and the refractive index on the vertical axis, and the plots were approximated by a straight line. A value of the refractive index at a point where this straight line was extrapolated to a point where the content rate of the powder reached 100% was defined as the refractive index of the powder.

The oil absorption per 100 g of the powder of Sample No. 4-1 was 57 ml/100 g as measured by a method according to JIS K 5101-13.

The MIU (average friction coefficient) was measured as the friction coefficient of the powder of Sample No. 4-1 using a friction tester "KES-SE" of KATO TECH CO., LTD. In the measurement, a double-sided tape was stuck onto a glass plate of a measuring table, and the powder was placed and fixed thereon. A 10 mm square silicon sensor was placed on this powder and moved under the conditions of a static load of 25 g and a scanning speed of 1 mm/sec, and then the MIU was measured within the range of 20 mm. As a result, the MIU was 0.98.

<Sample No. 4-2>

4 g of the powder of Sample No. 4-1 was placed in and mixed with 36 g of pure water, thereby obtaining a dispersion liquid of titanium phosphate plate-shaped particles. 2.60 g of an aqueous 48% sodium hydroxide solution was added to this dispersion liquid, mixed for 5 minutes, and then left to stand at room temperature (25° C.) for 2 hours. Next, suction filtration was performed to separate the solid content. The separated solid content was dried at 105° C. for 1 day. Thus, a powder of Sample No. 4-2 was obtained.

As a result of analyzing the powder of Sample No. 4-2 thus obtained using an X-ray diffractometer, it was found that the particles constituting the powder were crystalline sodium titanium phosphate having the rational formula of $Na_2Ti(PO_4)_2 \cdot H_2O$. When this powder was subjected to elemental analysis using an energy dispersive x-ray analysis (EDX) device, the presence of a sodium element (Na) was confirmed. More specifically, this powder is a powder containing the "plate-shaped particles derived from titanium phosphate containing a compound derived from titanium phosphate in which hydrogen of the titanium phosphate is replaced with alkali metal".

The powder of Sample No. 4-2 was also measured for the physical properties by the same methods as those for the powder of Sample No. 4-1. The values of the physical properties are as shown in Table 4. As shown in Table 4, the value of "Actual specific surface area/Assumed specific surface area" was 6.68.

When the powder of Sample No. 4-2 was observed with a scanning electron microscope, it was able to be confirmed that the particles constituting the powder had a plate shape and contained a large number of hexagonal plate-shaped particles as illustrated in FIG. 2A. Further, the formation of irregularities on the surface of the plate-shaped particles was also able to be confirmed as illustrated in FIG. 2B.

<Sample No. 4-3>

4 g of the powder of Sample No. 4-1 was placed in and mixed with 36 g of pure water, thereby obtaining a dispersion liquid of titanium phosphate plate-shaped particles. 3.65 g of an aqueous 48% potassium hydroxide solution was added to this dispersion liquid, mixed for 5 minutes, and then left to stand at room temperature (25° C.) for 2 hours. Next, suction filtration was performed to separate the solid content. The separated solid content was dried at 105° C. for 1 day. Thus, a powder of Sample No. 4-3 was obtained.

As a result of analyzing the powder of Sample No. 4-3 thus obtained using an X-ray diffractometer, it was found that the particles constituting the powder were almost the same as the crystalline titanium phosphate having the rational formula of $Ti(HPO_4)_2 \cdot H_2O$. When this powder was subjected to elemental analysis using an energy dispersive x-ray analysis (EDX) device, the presence of a potassium element (K) was confirmed. More specifically, this powder is a powder containing the "plate-shaped particles derived from titanium phosphate containing a compound derived from titanium phosphate in which alkali metal is contained in crystals of the titanium phosphate".

The powder of Sample No. 4-3 was also measured for the physical properties by the same methods as those for the powder of Sample No. 4-1. The values of the physical properties are as shown in Table 4. As shown in Table 4, the value of "Actual specific surface area/Assumed specific surface area" was 24.6.

When the powder of Sample No. 4-3 was observed with a scanning electron microscope, it was able to be confirmed that the particles constituting the powder had a plate shape and contained a large number of hexagonal plate-shaped particles as illustrated in FIG. 3A. Further, the formation of irregularities on the surface of the plate-shaped particles was also able to be confirmed as illustrated in FIG. 3B.

<Sample No. 4-4>

First, titanyl sulfate and phosphoric acid were reacted by a hydrothermal synthesis method, thereby manufacturing a titanium phosphate powder. The conditions of the hydrothermal synthesis were set as follows: the titanium concentration [Ti] of a raw material (mixture of titanyl sulfate and phosphoric acid) was set to 0.30 mol/L, the phosphorus concentration [P] was set to 3.22 mol/L, the concentration ratio thereof [P]/[Ti] was set to 11, the reaction temperature was set to 130° C., and the reaction time was set to 3 hours.

Specifically, first, titanyl sulfate as a titanium source and phosphoric acid as a phosphorus source were mixed, thereby obtaining a mixture. Next, the obtained mixture was placed in a reaction vessel (autoclave with a capacity of 200 L) and heated at 130° C. for 3 hours. At that time, the reaction vessel was not pressurized, and the pressure inside the vessel was set to a value naturally determined by the heating temperature (natural pressurization).

After 3 hours, a lid was opened to cool a slurry in the vessel to room temperature, the slurry was filtered, and then pure water was applied to a solid content remaining on a filter paper for cleaning. Next, pure water was added to the solid content after the cleaning to obtain a slurry, and 29% ammonium water (aqueous solution of ammonium salt) was added to the slurry until the pH reached 7. Next, the slurry was filtered, and then the same cleaning as above was performed to separate the solid content. The solid content was dried (left to stand at a temperature of 105° C. for 24 hours) to obtain a powder.

As a result of analyzing the powder of Sample No. 4-4 thus obtained using an X-ray diffractometer, it was able to be confirmed that the particles constituting the powder were crystalline titanium phosphate having the rational formula of $Ti(HPO_4)_2 \cdot H_2O$. More specifically, this powder is neither a powder containing the "plate-shaped particles derived from titanium phosphate containing a compound derived from titanium phosphate in which hydrogen of the titanium phosphate is replaced with alkali metal" nor a powder containing the "plate-shaped particles derived from titanium phosphate containing a compound derived from titanium phosphate in which alkali metal is contained in crystals of the titanium phosphate".

The powder of Sample No. 4-4 was also measured for the physical properties by the same methods as those for the powder of Sample No. 4-1. The values of the physical properties are as shown in Table 4. As shown in Table 4, the value of "Actual specific surface area/Assumed specific surface area" was 1.33.

When the powder of Sample No. 4-4 was observed with a scanning electron microscope, it was able to be confirmed that the particles constituting the powder had a plate shape and contained a large number of hexagonal plate-shaped particles as illustrated in FIG. 4A. Further, irregularities were not able to be confirmed on the surface of the plate-shaped particles as illustrated in FIG. 4B.

<Sample No. 4-5>

4 g of the powder of Sample No. 4-4 was placed in and mixed with 36 g of pure water, thereby obtaining a dispersion liquid of titanium phosphate plate-shaped particles. 2.60 g of an aqueous 48% sodium hydroxide solution was added to this dispersion liquid, mixed for 5 minutes, and then left to stand at room temperature (25° C.) for 2 hours. Next, suction filtration was performed to separate the solid content. The separated solid content was dried at 105° C. for 1 day. Thus, a powder of Sample No. 4-5 was obtained.

As a result of analyzing the powder of Sample No. 4-5 thus obtained using an X-ray diffractometer, it was found that the particles constituting the powder were crystalline sodium titanium phosphate having the rational formula of $Na_2Ti(PO_4)_2 \cdot H_2O$. When this powder was subjected to elemental analysis using an energy dispersive x-ray analysis (EDX) device, the presence of a sodium element (Na) was confirmed. More specifically, this powder is a powder containing the "plate-shaped particles derived from titanium phosphate containing a compound derived from titanium phosphate in which hydrogen of the titanium phosphate is replaced with alkali metal".

The powder of Sample No. 4-5 was also measured for the physical properties by the same methods as those for the powder of Sample No. 4-1. The values of the physical properties are as shown in Table 4. As shown in Table 4, the value of "Actual specific surface area/Assumed specific surface area" was 8.28.

When the powder of Sample No. 4-5 was observed with a scanning electron microscope, it was able to be confirmed that the particles constituting the powder had a plate shape and contained a large number of hexagonal plate-shaped particles as illustrated in FIG. 5A. Further, the formation of irregularities on the surface of the plate-shaped particles was also able to be confirmed as illustrated in FIG. 5B.

<Sample No. 4-6>

4 g of the powder of Sample No. 4-4 was placed in and mixed with 36 g of pure water, thereby obtaining a dispersion liquid of titanium phosphate plate-shaped particles. 3.65 g of an aqueous 48% potassium hydroxide solution was added to this dispersion liquid, mixed for 5 minutes, and then left to stand at room temperature (25° C.) for 2 hours. Next, suction filtration was performed to separate the solid content. The separated solid content was dried at 105° C. for 1 day. Thus, a powder of Sample No. 4-6 was obtained.

As a result of analyzing the powder of Sample No. 4-6 thus obtained using an X-ray diffractometer, it was found that the particles constituting the powder were almost the same as the crystalline titanium phosphate having the rational formula of $Ti(HPO_4)_2 \cdot H_2O$. When this powder was subjected to elemental analysis using an energy dispersive x-ray analysis (EDX) device, the presence of a potassium element (K) was confirmed. More specifically, this powder is a powder containing the "plate-shaped particles derived from titanium phosphate containing a compound derived from titanium phosphate in which alkali metal is contained in crystals of the titanium phosphate".

The powder of Sample No. 4-6 was also measured for the physical properties by the same methods as those for the powder of Sample No. 4-1. The values of the physical properties are as shown in Table 4. As shown in Table 4, the value of "Actual specific surface area/Assumed specific surface area" was 19.7.

When the powder of Sample No. 4-6 was observed with a scanning electron microscope, it was able to be confirmed that the particles constituting the powder had a plate shape and contained a large number of hexagonal plate-shaped particles as illustrated in FIG. 6A. Further, the formation of irregularities on the surface of the plate-shaped particles was also able to be confirmed as illustrated in FIG. 6B.

<Sample No. 4-7>

4 g of the powder of Sample No. 4-4 was placed in and mixed with 36 g of pure water, thereby obtaining a dispersion liquid of titanium phosphate plate-shaped particles. 1.65 g of a sodium carbonate powder was added to this dispersion liquid, mixed for 5 minutes, and then left to stand at room temperature (25° C.) for 2 hours. Next, suction filtration was performed to separate the solid content. The separated solid content was dried at 105° C. for 1 day. Thus, a powder of Sample No. 4-7 was obtained.

As a result of analyzing the powder of Sample No. 4-7 thus obtained using an X-ray diffractometer, it was found that the particles constituting the powder were crystalline sodium titanium phosphate having the rational formula of $Na_2Ti(PO_4)_2 \cdot H_2O$. When this powder was subjected to elemental analysis using an energy dispersive x-ray analysis (EDX) device, the presence of a sodium element (Na) was confirmed. More specifically, this powder is a powder containing the "plate-shaped particles derived from titanium phosphate containing a compound derived from titanium phosphate in which hydrogen of the titanium phosphate is replaced with alkali metal".

The powder of Sample No. 4-7 was also measured for the physical properties by the same methods as those for the powder of Sample No. 4-1. The values of the physical properties are as shown in Table 4. As shown in Table 4, the value of "Actual specific surface area/Assumed specific surface area" was 2.63.

When the powder of Sample No. 4-7 was observed with a scanning electron microscope, it was able to be confirmed that the particles constituting the powder had a plate shape and contained a large number of hexagonal plate-shaped particles as illustrated in FIG. 7A. Further, the formation of irregularities on the surface of the plate-shaped particles was also able to be confirmed as illustrated in FIG. 7B.

<Sample No. 4-8>

4 g of the powder of Sample No. 4-4 was placed in and mixed with 36 g of pure water, thereby obtaining a dispersion liquid of titanium phosphate plate-shaped particles. 2.16 g of a potassium carbonate powder was added to this dispersion liquid, mixed for 5 minutes, and then left to stand at room temperature (25° C.) for 2 hours. Next, suction filtration was performed to separate the solid content. The separated solid content was dried at 105° C. for 1 day. Thus, a powder of Sample No. 4-8 was obtained.

As a result of analyzing the powder of Sample No. 4-8 thus obtained using an X-ray diffractometer, it was found that the particles constituting the powder were almost the same as the crystalline titanium phosphate having the rational formula of $Ti(HPO_4)_2 \cdot H_2O$. When this powder was subjected to elemental analysis using an energy dispersive x-ray analysis (EDX) device, the presence of a potassium element (K) was confirmed. More specifically, this powder is a powder containing the "plate-shaped particles derived from titanium phosphate containing a compound derived from titanium phosphate in which alkali metal is contained in crystals of the titanium phosphate".

The powder of Sample No. 4-8 was also measured for the physical properties by the same methods as those for the powder of Sample No. 4-1. The values of the physical properties are as shown in Table 4. As shown in Table 4, the value of "Actual specific surface area/Assumed specific surface area" was 3.64.

When the powder of Sample No. 4-8 was observed with a scanning electron microscope, it was able to be confirmed that the particles constituting the powder had a plate shape and contained a large number of hexagonal plate-shaped particles as illustrated in FIG. 8A. Further, the formation of irregularities on the surface of the plate-shaped particles was also able to be confirmed as illustrated in FIG. 8B.

<Sample No. 4-9>

First, titanyl sulfate and phosphoric acid were reacted by a hydrothermal synthesis method, thereby manufacturing a titanium phosphate powder. The conditions of the hydrothermal synthesis were set as follows: the titanium concentration [Ti] of a raw material (mixture of titanyl sulfate and phosphoric acid) was set to 0.30 mol/L, the phosphorus concentration [P] was set to 3.93 mol/L, the concentration ratio thereof [P]/[Ti] was set to 13, the reaction temperature was set to 90° C., and the reaction time was set to 5 hours.

Specifically, first, titanyl sulfate as a titanium source and phosphoric acid as a phosphorus source were mixed, thereby obtaining a mixture. Next, the obtained mixture was placed in a reaction vessel (autoclave with a capacity of 1.4 L) and heated at 90° C. for 5 hours. At that time, the reaction vessel was not pressurized, and the pressure inside the vessel was set to a value naturally determined by the heating temperature (natural pressurization).

After 5 hours, a lid was opened to cool a slurry in the vessel to room temperature, the slurry was filtered, and then pure water was applied to a solid content remaining on a filter paper for cleaning. Next, pure water was added to the solid content after the cleaning to obtain a slurry, and 29% ammonium water (aqueous solution of ammonium salt) was added to the slurry until the pH reached 7. Next, the slurry was filtered, and then the same cleaning as above was performed to separate the solid content. The solid content was dried (left to stand at a temperature of 105° C. for 24 hours) to obtain a powder.

As a result of analyzing the powder of Sample No. 4-9 thus obtained using an X-ray diffractometer, it was able to be confirmed that the particles constituting the powder were crystalline titanium phosphate having the rational formula of $Ti(HPO_4)_2 \cdot H_2O$. More specifically, this powder is neither a powder containing the "plate-shaped particles derived from titanium phosphate containing a compound derived from titanium phosphate in which hydrogen of the titanium phosphate is replaced with alkali metal" nor a powder containing the "plate-shaped particles derived from titanium phosphate containing a compound derived from titanium phosphate in which alkali metal is contained in crystals of the titanium phosphate".

The powder of Sample No. 4-9 was also measured for the physical properties by the same methods as those for the powder of Sample No. 4-1.

The values of the physical properties are as shown in Table 4. As shown in Table 4, the value of "Actual specific surface area/Assumed specific surface area" was 0.93.

When the powder of Sample No. 4-9 was observed with a scanning electron microscope, it was able to be confirmed that the particles constituting the powder had a plate shape and contained a large number of hexagonal plate-shaped particles as illustrated in FIG. 9. Further, irregularities were not able to be confirmed on the surface of the plate-shaped particles.

<Sample No. 4-10>

4 g of the powder of Sample No. 4-9 was placed in and mixed with 36 g of pure water, thereby obtaining a dispersion liquid of titanium phosphate plate-shaped particles. 2.60 g of an aqueous 48% sodium hydroxide solution was added to this dispersion liquid, mixed for 5 minutes, and then left to stand at room temperature (25° C.) for 2 hours. Next, suction filtration was performed to separate the solid content. The separated solid content was dried at 105° C. for 1 day. Thus, a powder of Sample No. 4-10 was obtained.

As a result of analyzing the powder of Sample No. 4-10 thus obtained using an X-ray diffractometer, it was found that the particles constituting the powder were crystalline sodium titanium phosphate having the rational formula of $Na_2Ti(PO_4)_2 \cdot H_2O$. When this powder was subjected to elemental analysis using an energy dispersive x-ray analysis (EDX) device, the presence of a sodium element (Na) was confirmed. More specifically, this powder is a powder containing the "plate-shaped particles derived from titanium phosphate containing a compound derived from titanium phosphate in which hydrogen of the titanium phosphate is replaced with alkali metal".

The powder of Sample No. 4-10 was also measured for the physical properties by the same methods as those for the powder of Sample No. 4-1. The values of the physical properties are as shown in Table 4. As shown in Table 4, the value of "Actual specific surface area/Assumed specific surface area" was 1.57.

When the powder of Sample No. 4-10 was observed with a scanning electron microscope, it was able to be confirmed that the particles constituting the powder had a plate shape and contained a large number of hexagonal plate-shaped particles as illustrated in FIG. 10. Further, the formation of irregularities on the surface of the plate-shaped particles was also able to be confirmed.

The values of the physical properties of the powders are collectively shown in Table 4. Although the refractive indices of the powders of Samples No. 4-4 to No. 4-10 were not measured, it can be presumed that the values are almost the same as the refractive indices of the powders of Samples No. 4-1 to No. 4-3.

TABLE 4

| No. | pH | Whiteness | Average thickness (µm) | Average primary particle size (µm) | Aspect ratio | Refractive index | Oil absorption (ml/100 g) | Specific surface area (m²/g) Assumed | Specific surface area (m²/g) Actual | Specific surface area ratio (Actual/Assumed) | MIU |
|---|---|---|---|---|---|---|---|---|---|---|---|
| 4-1 | 3.6 | 94.6 | 0.44 | 3.72 | 8 | 1.73 | 57 | 2.22 | 2.83 | 1.27 | 0.98 |
| 4-2 | 6.9 | 94.9 | 0.47 | 3.74 | 8 | 1.79 | 57 | 2.11 | 14.1 | 6.68 | 0.93 |
| 4-3 | 6.5 | 95.7 | 0.48 | 3.71 | 8 | 1.76 | 77 | 2.08 | 51.1 | 24.6 | 0.90 |
| 4-4 | 3.7 | 98.4 | 0.77 | 6.97 | 9 | — | 47 | 1.26 | 1.67 | 1.33 | 0.92 |
| 4-5 | 7.1 | 97.1 | 0.80 | 6.95 | 9 | — | 46 | 1.22 | 10.1 | 8.28 | 0.95 |
| 4-6 | 7.0 | 96.4 | 0.80 | 6.95 | 9 | — | 56 | 1.22 | 24.0 | 19.7 | 0.89 |
| 4-7 | 5.6 | 98.0 | 0.79 | 6.98 | 9 | — | 47 | 1.23 | 3.24 | 2.63 | 0.94 |
| 4-8 | 5.9 | 95.0 | 0.80 | 6.95 | 9 | — | 50 | 1.22 | 4.44 | 3.64 | 0.83 |
| 4-9 | 2.3 | 96.9 | 0.029 | 0.25 | 9 | — | 100 | 33.8 | 31.4 | 0.93 | — |
| 4-10 | 6.8 | 99.5 | 0.031 | 0.23 | 7 | — | 97 | 32.7 | 51.5 | 1.57 | — |

As is understood from Table 4, the powders of Samples No. 4-2, No. 4-3, No. 4-5 to No. 4-8, and No. 4-10, which correspond to Examples of the second aspect of the present invention, are the powders containing plate-shaped particles derived from titanium phosphate containing any of the compound derived from titanium phosphate in which hydrogen of the titanium phosphate is replaced with alkali metal or the compound derived from titanium phosphate in which alkali metal is contained in crystals of the titanium phosphate, and these powders had the ratio (Actual specific surface area/Assumed specific surface area) of 1.5 or more.

In contrast thereto, the powders of Samples No. 4-1, No. 4-4, and No. 4-9, which correspond to Comparative Examples of the second aspect of the present invention, are not any of the powders containing plate-shaped particles derived from titanium phosphate described above but powders containing titanium phosphate plate-shaped particles, and these powders had the ratio (Actual specific surface area/Assumed specific surface area) of less than 1.5.

More specifically, the powders of Samples No. 4-2, No. 4-3, No. 4-5 to No. 4-8, and No. 4-10 have the ratio (Actual specific surface area/Assumed specific surface area) of 1.5 or more, and therefore the particles constituting the powders appropriately have surface irregularities and internal holes as compared with the powders of Samples No. 4-1, No. 4-4, and No. 4-9 having the ratio of less than 1.5. Hence, when used as a powder for cosmetic materials, a more refreshing feeling is obtained.

The powders of Samples No. 4-2 and No. 4-3 are not significantly different from the powder of Sample No. 4-1 in the whiteness, the average thickness, the average primary particle size, the aspect ratio, the refractive index, the assumed specific surface area, and the MIU and have values suitable as a powder for cosmetic materials. Similarly, the powders of Samples No. 4-5 to No. 4-8 are not significantly different from the powder of Sample No. 4-4 in the whiteness, the average thickness, the average primary particle size, the aspect ratio, and the assumed specific surface area and have values suitable as a powder for cosmetic materials. Similarly, the powder of Sample No. 4-10 is not significantly different from the powder of Sample No. 4-9 in the whiteness, the average thickness, the average primary particle size, the aspect ratio, and the assumed specific surface area and has values suitable as a powder for cosmetic materials.

The powders of Samples No. 4-2, No. 4-3, No. 4-5 to No. 4-8, and No. 4-10 are neutral, whereas the powders of Samples No. 4-1, No. 4-4, and No. 4-9 are acidic, and have properties (skin-friendly properties) preferable as a powder for cosmetic materials.

Fifth Example: Examples of Third Aspect

<Sample No. 5-1>

A powder of Sample No. 5-1 was prepared by the same method as that of Sample No. 4-1. The analysis results using an X-ray diffractometer, the observation results by a scanning electron microscope, and the physical properties of the obtained powder were the same as those of the powder of Sample No. 4-1.

The MIU (average friction coefficient) and the MMD (average deviation of friction coefficient: average value of variation values of the friction coefficient from the average friction coefficient) were measured as the friction coefficient using a friction tester "KES-SE" of KATO TECH CO., LTD. In the measurement, a double-sided tape was stuck onto a glass plate of a measuring table, and the powder was placed and fixed thereon. A 10 mm square silicon sensor was placed on this powder and moved under the conditions of a static load of 25 g and a scanning speed of 1 mm/sec, and then the MIU and the MMD was measured within the range of 20 mm. As a result, the MIU was 0.98 and the MMD was 0.010. Hence, the ratio (MMD/MIU) was 0.009.

<Sample No. 5-2>

A powder of Sample No. 5-2 was prepared by the same method as that of Sample No. 4-2. The analysis results using an X-ray diffractometer, the observation results by a scanning electron microscope, and the physical properties of the obtained powder were the same as those of the powder of Sample No. 4-2.

The values of the physical properties are as shown in Table 5. As shown in Table 5, the ratio (MMD/MIU) was 0.013.

<Sample No. 5-3>

A powder of Sample No. 5-3 was prepared by the same method as that of Sample No. 4-3. The analysis results using an X-ray diffractometer, the observation results by a scanning electron microscope, and the physical properties of the obtained powder were the same as those of the powder of Sample No. 4-3.

The values of the physical properties are as shown in Table 5. As shown in Table 5, the ratio (MMD/MIU) was 0.016.

<Sample No. 5-4>

A powder of Sample No. 5-4 was prepared by the same method as that of Sample No. 4-4. The analysis results using an X-ray diffractometer, the observation results by a scanning electron microscope, and the physical properties of the obtained powder were the same as those of the powder of Sample No. 4-4.

The values of the physical properties are as shown in Table 5. As shown in Table 5, the ratio (MMD/MIU) was 0.008.

<Sample No. 5-5>

A powder of Sample No. 5-5 was prepared by the same method as that of Sample No. 4-6. The analysis results using an X-ray diffractometer, the observation results by a scanning electron microscope, and the physical properties of the obtained powder were the same as those of the powder of Sample No. 4-6.

The values of the physical properties are as shown in Table 5. As shown in Table 5, the ratio (MMD/MIU) was 0.013.

<Sample No. 5-6>

A powder of Sample No. 5-6 was prepared by the same method as that of Sample No. 4-7. The analysis results using an X-ray diffractometer, the observation results by a scanning electron microscope, and the physical properties of the obtained powder were the same as those of the powder of Sample No. 4-7.

The values of the physical properties are as shown in Table 5. As shown in Table 5, the ratio (MMD/MIU) was 0.011.

The values of the physical properties of the powders are collectively shown in Table 5. Although the refractive indices of the powders of Samples No. 5-4 to No. 5-6 were not measured, it can be presumed that the values are almost the same as the refractive indices of the powders of Samples No. 5-1 to 5-3.

priately have surface irregularities and internal holes as compared with the powders of Samples No. 5-1 and No. 5-4 having the ratio of less than 1.5. As a result, the MMD is higher, and thus a more refreshing feeling is obtained when used as a powder for cosmetic materials.

The powders of Samples No. 5-2, No. 5-3 are not significantly different from the powder of Sample No. 5-1 in the whiteness, the average thickness, the average primary particle size, the aspect ratio, the refractive index, the assumed specific surface area, and the MIU and have values suitable as a powder for cosmetic materials. Similarly, the powders of Samples No. 5-5, No. 5-6 are not significantly different from the powder of Sample No. 5-4 in the whiteness, the average thickness, the average primary particle size, the aspect ratio, the assumed specific surface area, and the MIU and have values suitable as a powder for cosmetic materials.

The powders of Samples No. 5-2, No. 5-3, No. 5-5, and No. 5-6 are neutral, whereas the powders of Samples No. 5-1 and No. 5-4 are acidic, and have properties (skin-friendly properties) preferable as a powder for cosmetic materials.

The powders of Samples No. 5-2 and No. 5-3 have the MIU similar to that of the powder of Sample No. 5-1, and therefore can maintain slipperiness and were very rough due to the large MMD. The friction coefficient ratios (MMD/MIU) of the powders of Samples No. 5-2 and No. 5-3 were 0.011 or more. Hence, when used as a powder for cosmetic materials, not only good slipperiness but a refreshing feeling can be obtained.

TABLE 5

| No. | pH | White-ness | Average thickness (μm) | Average primary particle size (μm) | Aspect ratio | Refrac-tive index | Oil absorption (ml/100 g) | Specific surface area $(m^2/g)$ Assumed | Specific surface area $(m^2/g)$ Actual | Specific surface area ratio (Actual/Assumed) | MIU | MMD | MMD/MIU |
|---|---|---|---|---|---|---|---|---|---|---|---|---|---|
| 5-1 | 3.6 | 94.6 | 0.44 | 3.72 | 8 | 1.73 | 57 | 2.22 | 2.83 | 1.27 | 0.98 | 0.009 | 0.009 |
| 5-2 | 6.9 | 94.9 | 0.47 | 3.74 | 8 | 1.79 | 57 | 2.11 | 14.1 | 6.68 | 0.93 | 0.012 | 0.013 |
| 5-3 | 6.5 | 95.7 | 0.48 | 3.71 | 8 | 1.76 | 77 | 2.08 | 51.1 | 24.6 | 0.90 | 0.014 | 0.016 |
| 5-4 | 3.7 | 98.4 | 0.77 | 6.97 | 9 | — | 47 | 1.26 | 1.67 | 1.33 | 0.92 | 0.007 | 0.008 |
| 5-5 | 7.0 | 96.4 | 0.80 | 6.95 | 9 | — | 56 | 1.22 | 24.0 | 19.7 | 0.89 | 0.012 | 0.013 |
| 5-6 | 5.6 | 98.0 | 0.79 | 6.98 | 9 | — | 47 | 1.23 | 3.24 | 2.63 | 0.94 | 0.010 | 0.011 |

As is understood from Table 5, the powders of Samples No. 5-2, No. 5-3, No. 5-5, and No. 5-6, which correspond to Examples of the third aspect of the present invention, are the powders containing plate-shaped particles derived from titanium phosphate containing any of the compound derived from titanium phosphate in which hydrogen of the titanium phosphate is replaced with alkali metal or the compound derived from titanium phosphate in which alkali metal is contained in crystals of the titanium phosphate, and these powders had the ratio (Actual specific surface area/Assumed specific surface area) of 1.5 or more.

In contrast thereto, the powders of Samples No. 5-1 and No. 5-4, which correspond to Comparative Examples of the third aspect of the present invention, are not any of the powders containing plate-shaped particles derived from titanium phosphate described above but powders containing titanium phosphate plate-shaped particles, and these powders had the ratio (Actual specific surface area/Assumed specific surface area) of less than 1.5.

More specifically, the powders of Samples No. 5-2, No. 5-3, No. 5-5, and No. 5-6 have the ratio (Actual specific surface area/Assumed specific surface area) of 1.5 or more, and therefore the particles constituting the powders appro- The powders of Samples No. 5-5 and No. 5-6 have the MIU similar to that of the powder of Sample No. 5-4, and therefore can maintain slipperiness and were very rough due to the large MMD. The friction coefficient ratios (MMD/MIU) of the powders of Samples No. 5-5 and No. 5-6 were 0.011 or more. Hence, when used as a powder for cosmetic materials, not only good slipperiness but a refreshing feeling can be obtained.

The invention claimed is:

1. A powder comprising:

plate-shaped particles derived from titanium phosphate containing any of a compound derived from titanium phosphate in which hydrogen of the titanium phosphate is replaced with alkali metal or a compound derived from titanium phosphate in which alkali metal is contained in crystals of the titanium phosphate, wherein a ratio of an average deviation of a friction coefficient (MMD) to an average friction coefficient (MIU) (MMD/MIU) is 0.011 or more, and wherein the plate-shaped particles derived from titanium phosphate comprise $Ti(HPO_4)_2 \cdot H_2O$ or $Na_2Ti(PO_4)_2 \cdot H_2O$.

2. The powder according to claim 1, wherein the plate-shaped particles derived from titanium phosphate are hexagonal plate-shaped particles.

3. The powder according to claim 1, wherein an average thickness of the plate-shaped particles derived from titanium phosphate is 0.01 μm or more and 4 μm or less, and an aspect ratio is 5 or more, the aspect ratio being a value obtained by dividing an average primary particle diameter of the plate-shaped particles derived from titanium phosphate by the average thickness.

4. A method for increasing a specific surface area of titanium phosphate plate-shaped particles comprising:

obtaining a liquid in a state where the powder of claim 1 is dispersed in an aqueous alkaline solution.

5. The method for increasing a specific surface area of titanium phosphate plate-shaped particles according to claim 4, wherein the titanium phosphate plate-shaped particles are hexagonal plate-shaped particles.

6. The method for increasing a specific surface area of titanium phosphate plate-shaped particles according to claim 1, wherein the liquid has a pH value around neutrality.

7. The method for increasing a specific surface area of titanium phosphate plate-shaped particles according to claim 6, wherein an average thickness of the titanium phosphate plate-shaped particles is 0.01 μm or more and 4 μm or less, and an aspect ratio is 5 or more, the aspect ratio being a value obtained by dividing an average primary particle diameter of the titanium phosphate plate-shaped particles by the average thickness.

8. The method for increasing a specific surface area of titanium phosphate plate-shaped particles according to claim 6, wherein the titanium phosphate plate-shaped particles are hexagonal plate-shaped particles.

9. The method for increasing a specific surface area of titanium phosphate plate-shaped particles according to claim 1, wherein an average thickness of the titanium phosphate plate-shaped particles is 0.01 μm or more and 4 μm or less, and an aspect ratio is 5 or more, the aspect ratio being a value obtained by dividing an average primary particle diameter of the titanium phosphate plate-shaped particles by the average thickness.

10. The method for increasing a specific surface area of titanium phosphate plate-shaped particles according to claim 9, wherein the titanium phosphate plate-shaped particles are hexagonal plate-shaped particles.

11. The method for increasing a specific surface area of titanium phosphate plate-shaped particles according to claim 9, wherein the average primary particle diameter is 0.05 μm or more and 20 μm or less.

12. The method for increasing a specific surface area of titanium phosphate plate-shaped particles according to claim 11, wherein the titanium phosphate plate-shaped particles are hexagonal plate-shaped particles.

\* \* \* \* \*